United States Patent
Shioda

(10) Patent No.: US 10,123,692 B2
(45) Date of Patent: Nov. 13, 2018

(54) OPHTHALMOLOGIC APPARATUS AND CONTROL METHOD THEREFOR

(71) Applicant: CANON KABUSHIKI KAISHA, Tokyo (JP)

(72) Inventor: Hayato Shioda, Chigasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 350 days.

(21) Appl. No.: 14/696,574

(22) Filed: Apr. 27, 2015

(65) Prior Publication Data

US 2015/0313469 A1    Nov. 5, 2015

(30) Foreign Application Priority Data

May 2, 2014    (JP) ................. 2014-095266

(51) Int. Cl.
| | | |
|---|---|---|
| A61B 3/00 | (2006.01) | |
| A61B 3/15 | (2006.01) | |
| A61B 3/12 | (2006.01) | |
| A61B 3/14 | (2006.01) | |

(52) U.S. Cl.
CPC .............. *A61B 3/0075* (2013.01); *A61B 3/12* (2013.01); *A61B 3/152* (2013.01); *A61B 3/14* (2013.01)

(58) Field of Classification Search
CPC ......... A61B 3/0075; A61B 3/12; A61B 3/152; A61B 3/14
USPC ........................................................ 351/208
See application file for complete search history.

(56) References Cited

U.S. PATENT DOCUMENTS

| 7,703,920 B2 | 4/2010 | Isogai et al. |
| 2009/0195750 A1 | 8/2009 | Isogai et al. |

FOREIGN PATENT DOCUMENTS

| JP | H04-338447 A | 11/1992 |
| JP | H07-194535 A | 8/1995 |
| JP | 2001-275973 A | 10/2001 |
| JP | 2003-010121 A | 1/2003 |
| JP | 2009-201981 A | 9/2009 |
| JP | 2013-027537 A | 2/2013 |

*Primary Examiner* — William R Alexander
*Assistant Examiner* — Wen Huang
(74) *Attorney, Agent, or Firm* — Fitzpatrick, Cella, Harper & Scinto

(57) ABSTRACT

An ophthalmologic apparatus wherein auto alignment and manual alignment can be selectively used to enhance alignment accuracy between an eye to be inspected and an ophthalmic part includes an ophthalmic part that detects an eye to be inspected, a fixing part, a movable part on which the ophthalmic part is placed and configured to be movable with respect to the fixing unit in a horizontal direction, a drive part that transmits electric drive force for horizontal movement of the movable part, an alignment detection unit that detects a relative position between the eye to be inspected and ophthalmic part, a controller that controls the movable part based on a detection result from the alignment detection unit, and a drive force transmit switching unit that switches whether or not to execute transmission of the drive force from the drive part to the movable part.

18 Claims, 10 Drawing Sheets

OPHTHALMOLOGIC APPARATUS AND CONTROL METHOD THEREFOR

BACKGROUND OF THE INVENTION

Field of the Invention

The present invention relates to an ophthalmologic apparatus, a fundus camera for photographing and observing an eye to be inspected and a control method therefor.

Description of the Related Art

An ophthalmologic apparatus, particularly, a fundus camera for photographing and observing an eye to be inspected needs to align an ophthalmic part with a predetermined position with respect to the eye to be inspected. Conventionally, there is known an ophthalmologic apparatus having a slide mechanism that mechanically moves, through manual operation of a joystick by an inspector, a movable part on which the ophthalmic part is placed in a horizontal direction with respect to a fixing part. Further, there is known an ophthalmologic apparatus wherein a drive mechanism capable of moving the ophthalmic part in forward-backward, left-right and up-down directions is provided on such a movable part so as to enable automatic alignment (see Japanese Patent Application Laid-Open No. 2009-201981).

A so-called auto alignment where alignment is automatically performed can achieve alignment in a shorter time than manual alignment. However, when an eye to be inspected to be photographed is large in involuntary eye movement, the ophthalmic part moved by the drive mechanism may fail to follow the movement of the eye to be inspected. In such a case, the eye to be inspected may fail to be photographed properly in the auto alignment. Further, when the eye to be inspected is to diseased eye that cannot be photographed properly even when alignment is made on a pupil center, minute operation is required for the alignment. In such a case, manual alignment using an electric alignment operation member (electric joystick, trackball, etc.) has poor operability, which may take a lot of time and trouble to achieve alignment.

As a counter measure, an operation sequence can be considered, in which alignment up to the pupil center for which minute operation is not required is performed with the auto alignment and, thereafter, minute manual alignment using a mechanical slide mechanism and an alignment operation member is performed if minute operation is required. Therefore, a configuration in which the above operation sequence can be executed is desired.

For execution of the above operation sequence in a conventional ophthalmologic apparatus, a two-stage movable part configuration in which an electric movable part is placed on a mechanical movable part is required. However, in such a two-stage configuration, the electric movable part may be positioned close to an eye to inspected side (left or right eye). In this state, it is necessary to take into consideration that a gravity center or ophthalmic part is offset with respect to the mechanical movable part.

SUMMARY OF THE INVENTION

The present invention has been made in view of the above situation, and an object thereof is to provide an ophthalmologic apparatus having a movable part including a plurality of movement modes wherein the movement modes can be appropriately operated within their individual movable ranges without being affected by the above-mentioned offset of the gravity center and a control method therefor.

To achieve the above object, according to the present invention, there is provided an ophthalmologic apparatus including a movable part having an ophthalmic part and configured to be movable with respect to a fixing unit in a horizontal direction, a drive part that transmits electric drive force for horizontal movement of the movable part, and a drive force transmit switching unit that switches whether or not to execute transmission of the electric drive force from the drive part to the movable part.

According to the present invention, even an a movable part including a plurality of movement modes, the movement modes can be appropriately operated within their individual movable ranges.

Further features of the present invention will become apparent from the following description of exemplary embodiments with reference to the attached drawings.

BRIEF DESCRIPTION OF THE DRAWINGS

FIGS. 1A and 1B are exemplary views illustrating an entire configuration of a fundus camera according to a first embodiment of the present invention, in which FIG. 1A is a partial side perspective view, and FIG. 1B is a partial plan perspective view.

DESCRIPTION OF THE EMBODIMENTS

Preferred embodiments of the present invention will now be described in detail in accordance with the accompanying drawings.

First Embodiment

Details of a fundus camera according to an embodiment of the present invention will be described based on FIGS. 1A to 10.

Figure 1A:
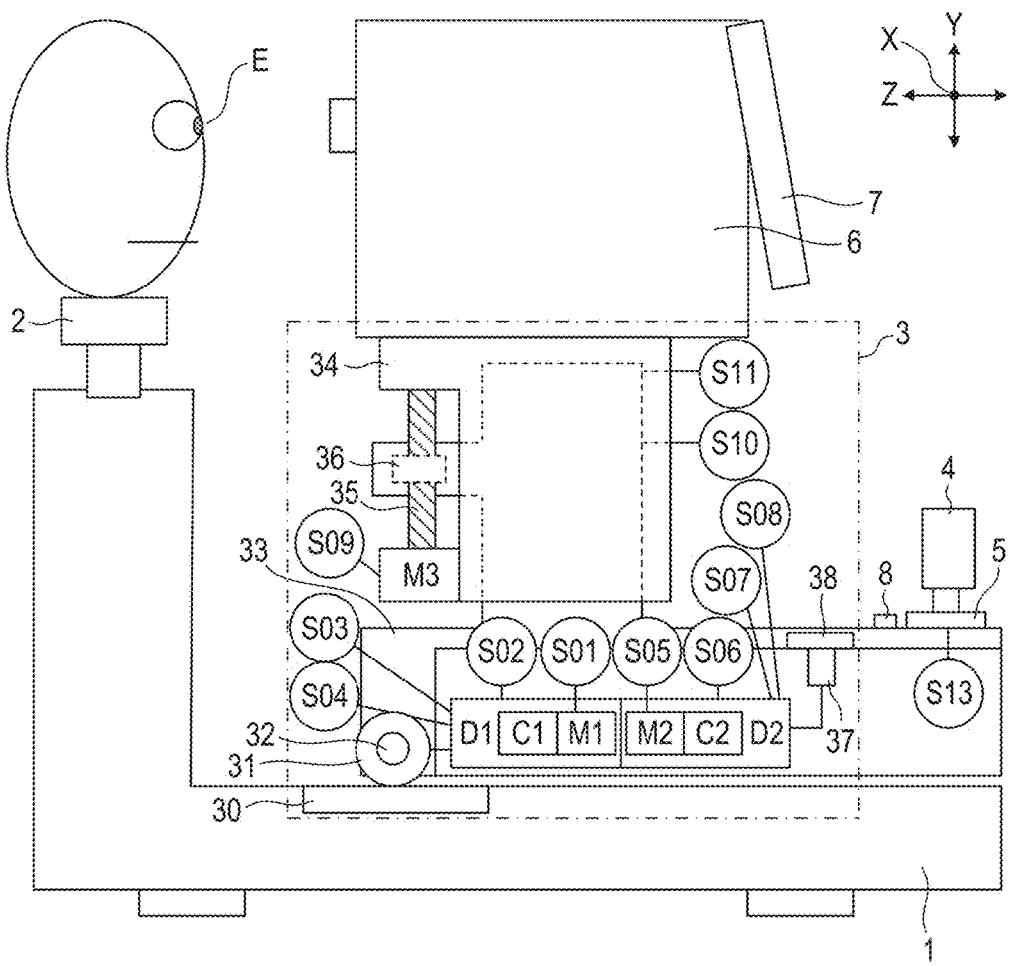
Figure 1B:
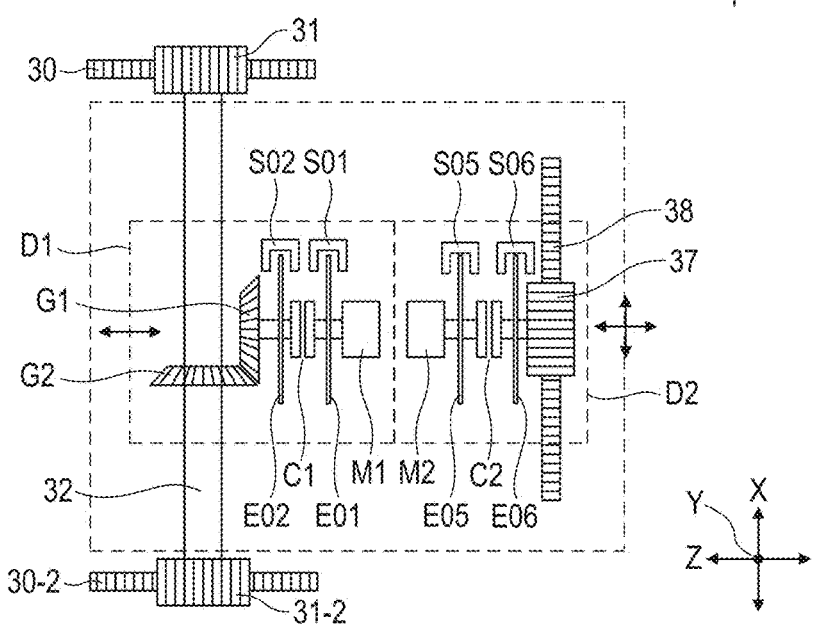

FIG. 1A is a view illustrating an entire configuration of the fundus camera of a first embodiment. FIG. 1B is an exemplary plan view illustrating a configuration of a Z drive part to be described later.

The fundus camera illustrated in FIGS. 1A and 1B mainly includes a fixing part 1, a chin receiver 2, a movable part 3, an alignment operation member 4, a focus operation member 5, an ophthalmic part 6, a display part 7, and a mode switching switch 8. The fixing part 1 as a fixing unit has the chin receiver 2 for supporting a chin of a subject. The movable part 3 as a movable unit is movably supported by the fixing part 1 and has the ophthalmic part 6 placed thereon. The alignment operation member 4, focus operation member 5, ophthalmic part 6, and mode switching switch 8 are provided in the movable part 3, while the display part 7 is provided in the ophthalmic part 6. The ophthalmic part 6 as an examination unit has disposed therein various optical systems to be described later used for irradiation of observation light to an eye E to be inspected and observation/photographing of the eye E to be inspected. The display part 7 is a touch panel and can be used as an interface for operation and setting of the fundus camera.

The mode switching switch 8 is a switch for switching between a full manual mode, a semi-auto mode, and a full auto mode. These modes are switched every time the mode switching switch 8 is depressed. Details of these modes will be described in conjunction with a flowchart to be described later. The alignment operation member 4 is used for alignment between the eye E to be inspected and ophthalmic part 6. Specifically, in the present embodiment, the alignment operation member 4 is operated to move the movable part 3 horizontally and vertically on the fixing part 1. Although the display part 7 is provided in the ophthalmic part 6 in the present embodiment, it may be provided in the fixing part 1 or movable part 3. Further, although the mode switching switch 8 is provided in the movable part 3 in the present embodiment, it may be provided in one of the alignment operation member 4, ophthalmic part 6, and display part 7. Alternatively, the mode switching switch 8 may be provided at a plurality of positions.

[XYZ Movable Part]

The movable part 3 is made movable in forward-backward and left-right directions on the fixing part 1 by a known slide mechanism represented by a combination of a sliding shaft and a linear bush. A left-right (X) direction corresponds to a direction perpendicular to a paper surface of FIG. 1A which is a width direction of the eye E to be inspected, and a forward-backward (Z) direction corresponds to a left-right direction in FIG. 1A which is a direction approaching or separating from the eye E to be inspected. Thus, a horizontal direction in the present embodiment is a direction in a horizontal plane defined by the X-direction which is the width direction of the eye E to be inspected and Z-direction which is the direction approaching or separating from the eye E to be inspected. Further, the ophthalmic part 6 is made movable in an up-down (Y) direction (up-down direction in FIG. 1A) with respect to the fixing part 1 by a known drive mechanism represented by a combination of a drive source (motor), a deceleration mechanism, a rotary motion-linear motion conversion mechanism (a feed screw and a nut), and a slide mechanism. The drive mechanism is preferably provided in the movable part 3 and constitutes a Y-direction movable unit of the present embodiment that moves the examination unit in the Y-direction perpendicular to a horizontal plane. With the above configuration, through the movable part 3, the ophthalmic part 6 can be moved three-dimensionally (in X-, Y-, and Z-directions) with respect to the fixing part 1, enabling alignment with the eye E to be inspected.

Further, the movable part 3 has a drive part that can transmit electric drive force to a slide mechanism slidable in the X and Z directions. Operating a drive force transmit switching unit provided in the drive part as a drive unit allows switching whether or not drive force from a motor is transmitted to the slide mechanism.

In a state where drive force of the drive part is not transmitted to the slide mechanism according to the setting of the drive force transmit switching unit, the slide mechanism is used as a manual movement mechanism for horizontally moving the movable part 3 through an inspector's manual operation with respect to the alignment operation member 4 provided in the movable part 3. As a typical alignment operation member 4, a joystick is exemplified. Details of the alignment operation member 4 will be described later.

On the other hand, in a state where drive force of the drive part is transmitted to the slide mechanism according to the setting of the drive force transmit switching unit, the slide mechanism is used as an electric movement mechanism for horizontally moving the movable part 3 by means of the drive force from the drive part.

The following describes details of the (XZ) slide mechanism, a Z drive part, an X drive part, and a Y drive mechanism in the movable part 3.

[Slide Mechanism]

The slide mechanism according to the present embodiment has two rack gears 30 and 30-2, two gears 31 and 31-2, a shaft 32, and an XZ frame 33 at both ends of the fixing part 1 in the X-direction. The two rack gears 30 and 30-2 are provided at both ends of the fixing part 1 in the X-direction, respectively. The rack pears 30 and 30-2 are engaged with the gears 31 and 31-2, respectively. The gears 31 and 31-2 are fitted to both ends of the shaft 32. The shaft 32 is fitted to the XZ frame 33 through a linear bush and a bearing (which are not illustrated) so as to be rotationally and linearly slidable.

When the XZ frame 33 receives Z-direction force through the inspector's manual operation with respect to the alignment operation member 4, the shaft 32 is rotationally slid with respect to the XZ frame 33 through the bearing. With the rotational slide, the gears 31 and 31-2 roll on their corresponding rack gears 30 and 30-2 together with the shaft 32, causing the movable part 3 to move in the Z-direction. Further, when the XZ frame 33 receives X-direction force through the inspector's manual operation with respect to the alignment operation member 4, the XZ frame 33 is linearly slid with respect to the shaft 32 through the linear bush, causing the movable part 3 to move in the X-direction.

In the present embodiment described above, a slit lamp with a known slide mechanism is used; however, the present invention is not limited to this, and various types of configurations may be adopted as long as a horizontally-movable slide mechanism is used.

[Z Drive Part]

A Z drive part D1 illustrated in FIG. 1B has a Z motor M1, an encoder E01, a Z driving amount detection sensor S01, a not illustrated deceleration mechanism, a Z electromagnetic clutch C1, a Z drive part final stage gear G1, an encoder E02, a Z moving amount detection sensor S02, a Z reference position detection sensor S03, and a Z limit detection sensor S04. The encoder E01 is rotated in sync with the Z motor M1. The Z driving amount detection sensor S01 detects rotation (Z motor driving amount) of the encoder E01. The Z drive part final stage gear G1 is provided on an operation side with respect to the Z electromagnetic clutch C1. The Z moving amount detection sensor S02 detects rotation of the encoder E02 provided on the Z drive part final stage gear G1 to thereby detect a Z-direction moving amount of the movable part 3. The Z reference position detection sensor S03 such as a photointerrupter/slit plate detects that the movable part 3 is situated at a Z reference position. The Z limit detection sensor S04 such as a photointerrupter/slit plate detects a Z auto limit position of the movable part 3. Further, the shaft 32 is rotationally slidably fitted to the Z drive part D1 through a not illustrated bearing.

The Z or part final stage gear G1 is engaged with a gear G2 fitted to the shaft 32 to transmit drive force from the Z motor M1 to the slide mechanism. When the Z motor M1 is driven, the shaft 32 is rotated through the not illustrated deceleration mechanism, Z electromagnetic clutch C1, Z drive part final stage gear G1, and gear G2. When the shaft 32 is rotated, the gears 31 and 31-2 fitted to the shaft 32 roll while being engaged with the rack gears 30 and 30-2 fitted to the fixing part 1. As a result, the movable part 3 is moved in the Z-direction by electric drive. At the same time, the Z drive part D1 is moved in the Z-direction together with the movable part 3. The two rack gears 30 and 30-2 whose gear phases are matched play a role of a Z-direction linear guide.

[X Drive Part]

A X drive part D2 illustrated in FIG. 1B has a X motor M2, an encoder E05, an X driving amount detection sensor S05, a not illustrated deceleration mechanism, an X electromagnetic clutch C2, an X drive part final stage gear 37, an encoder E06, an X driving amount detection sensor S06, an X reference position detection sensor S07, and an X limit detection sensor S08. The encoder E05 is rotated in sync with the X motor M2. The X driving amount detection sensor S05 detects rotation (X motor driving amount) of the encoder E05. The X drive part final stage gear 37 is provided on an operation side with respect to the X electromagnetic clutch C2. The X driving amount detection sensor S06 detects rotation of the encoder E06 provided on the X drive part final stage gear 37 to thereby detect an X-direction moving amount of the movable part 3. The X reference position detection sensor S07 such as a photointerrupter/slit plate detects that the movable part 3 is situated at an X reference position. The X limit detection sensor S08 such as a photointerrupter/slit plate detects an X auto limit position of the movable part 3. The X drive part D2 is fitted to the Z drive part D1.

The X drive part final stage gear 37 is engaged with a rack gear 38 fitted to the XZ frame 33 to transmit drive force from the X motor M2 to the slide mechanism. When the X motor M2 is driven, the X drive part final stage gear 37 is rotated through the not illustrated deceleration mechanism and X electromagnetic clutch C2. The X drive part final stage gear 37 rolls while being engaged with the rack gear 38 fitted to the XZ frame 33. As a result the movable part 3 is moved in the X-direction by electric drive. At the same time, the X drive part D2 is integrated with the Z drive part D1 and is thud not moved in the X-direction. The shaft 32 plays a role of a linear guide.

In the present embodiment, the electromagnetic clutch is used as the drive force transmit switching unit; alternatively, however, a configuration may be adopted, in which a drive source for mechanical clutch switching is provided separately from the Z motor M1 and X motor M2, and a mechanical clutch such as a dog clutch is used.

[Y Drive Mechanism]

The Y drive mechanism has a Y motor M3, a Y driving amount detection sensor S09, a Y frame 34, a Y feed screw 35, a Y nut 36, a Y reference detection sensor S10, and Y limit detection sensor S11. The Y driving amount detection sensor S09 detects a driving amount of the Y motor M3. The Y motor M3 is fitted to the Y frame 34. The Y feed screw 35 is connected to a Y motor output shaft, and the Y nut 36 is fixed to the XZ frame 33 so as to be movable on the Y feed screw 35 in the Y-direction. The Y reference detection sensor S10 such as a photointerrupter/slit plate detects that the movable dart 3 is situated at a Y reference position. The Y limit detection sensor S11 such as a photointerrupter/slit plate detects a Y auto limit position of the movable part 3.

When the Y motor M3 is driven, the Y frame 34 is moved, through the Y feed screw 35 and Y nut 36, relative to the XZ frame 33 in the Y-direction by electric drive.

The slide mechanism has a fitting gap at each slide part and thus generates an eccentricity between a photographing optical axis and a pupil center. For example, in a case of the fundus camera described in the first embodiment, it is preferable to suppress a photographing optical axis eccentric amount to 0.4 mm or less in order to prevent a flare from occurring in a photographing image. In the present embodiment in which the auto alignment and manual alignment is realized by one-stage movable part configuration, a total fitting gap of XYZ slide mechanism slide parts is reduced as compared to that in the two-stage movable part configuration. Thus, it is possible to suppress the photographing optical axis eccentric amount to 0.2 mm or less.

[XZ Position Detection/XZ Position Control]

The following describes a method of detecting the reference position and auto limit position in the XYZ-directions and XYZ position control. XZ position detection of the movable part 3 is performed using the above-mentioned sensors S01 to S08.

In a state where drive force of the drive part is not transmitted to the slide mechanism according to the setting of the drive force transmit switching unit, even when the movable part 3 is horizontally moved by the inspector's manual operation with respect to the alignment operation member 4, only the gear on the operation side with respect to the drive force transmit switching unit is rotated. Thus, the motor shaft is not rotated, making it impossible for the driving amount detection sensors S01 and S05 to grasp a position of the movable part 3. So, when the eye E to be inspected is not detected by an anterior ocular segment observation optical system to be described later, a system controller 100 (see FIG. 4) to be described later roughly controls an absolute position of the movable part 3 based on outputs of the moving amount detection sensors S02 and S06 with the reference detection sensors S03 and S07 as reference positions. In this case, the moving amount detection sensors and a module region that obtains the absolute position in the system controller 100 constitute an absolute position detection unit that detects the absolute position of the movable part 3 in the present embodiment.

On the other hand, when the eye E to be inspected is detected, the system controller 100 finely controls a relative position of the movable part 3 based on outputs of the driving amount detection sensors S01 and S05 with the absolute position of the movable part 3 obtained when the eye E to be inspected is detected, that is, when an image is obtained as a reference position. The reference detection sensors S03 and S07 are preferably provided near a center of a movable range of the movable part 3. In this case, the moving amount detection sensors and a module region that obtains the relative position in the system controller 100 constitute a relative position detection unit that detects the relative position of the movable part 3 in the present embodiment.

The present embodiment includes the deceleration mechanism, so that the moving amount detection sensors S02 and S06 are lower in detection resolution than the driving amount detection sensors S01 and S05. For example, in the case of the fundus camera described in the first embodiment, required stop accuracy for the movable part 3 upon photographing is 0.2 mm. For achievement of the required accuracy, the detection resolution of the driving amount detection sensors S01 and S05 is set to 0.1 mm, and detection resolution of the moving amount detection sensors S02 and S06 is set to about 0.5 mm.

The system controller 100 controls the absolute position of the movable part 3 based on outputs of the moving amount detection sensors S02 and S06 with the reference detection sensors S03 and S07 as references. However, a movable limit during electric drive is influenced by a displacement due to an external factor or a failure. To cope with this, the limit detection sensors S04 and S08 are provided in the present embodiment. This prevents the movable part 3 from being moved outside a detection range of the limit detection sensor during electric drive and, when the movable part 3 is situated outside the detection range of the limit detection sensor before electric drive, the system controller 100 controls the movable part 3 to move inside the movable range. A movable range of the movable part 3 when the movable part 3 is moved through the inspector's manual operation is set wider than the detection range of each of the limit detection sensors S04 and S08. Thus, it is preferable to provide an elastic body at a mechanical contact portion at the movable limit.

Mechanical elements, such as gears, that move while being engaged with each other need to have a gap in the movement direction so as to be freely movable. The gap is provided also between a feed screw and a nut in a feed screw mechanism or a nut and a nut cover. Such a gap is called a backlash. The movable part 3 has the backlash in the deceleration mechanism (gear, etc.) of the drive part, drive force transmit switching unit (clutch, etc.), and rotary motion-linear motion conversion mechanism (rack/pinion, etc.). However, when the above gap is eliminated by biasing of a spring or the like, manual operability is affected.

In order to cope with this, in the present embodiment, the movable part 3 is reciprocated by an arbitrary amount from the reference detection sensors S03 and S07, and a backlash amount is measured based on difference between the moving amount and detection results of the driving amount detection sensors S01 and S05 and stored in the system controller 100. As a result, when the movement direction of the movable part 3 is reversed during electric drive, a driving amount of the movable part 3 is increased by an amount corresponding to the stored backlash amount, whereby the displacement due to backlash can be eliminated.

The above feedback control need not be performed during the absolute position control. There is no problem as long as the feedback control is performed while the eye to be inspected is being detected, that is, during the relative position control. With regard to the Y-direction, the movable part 3 is biased downward by a weight of the ophthalmic part 6, so that the above feedback control is not applied.

The backlash amount may be measured by reciprocation of the movable part 3 between both ends of the movable range using the limit detection sensors S04 and S08. Alternatively, the backlash amount may be measured by reciprocation of the movable part 3 between the reference detection sensors S03, S07 and limit detection sensors S04, S08. Further alternatively, the backlash amount may be calculated from a driving amount and the number of times of reversal during a time from when the movable part 3 passes through the reference detection sensors S03 and S07 until it passes through the reference detection sensors S03 and S07 once again in a case where, for example, eye E to be inspected is switched from the left eye to the right eye or vice-versa. The backlash amount may be changed with time, it is preferably newly stored every time the device is activated.

[Y Position Detection/Y Position Control]

Y position detection of the movable part 3 is performed using the above-mentioned sensors S09 to S11. The system controller 100 finely controls the relative position of the movable part 3 based on an output of the driving amount detection sensor S09 with the reference detection sensor S10 as a reference position. The reference detection sensor S10 is preferably provided near the center of the movable range of the movable part 3.

Further, the system controller 100 controls the relative position of the movable part 3 based on the output of the driving amount detection sensor S09 with reference detection sensor S10 as a reference. In the present embodiment, with respect to the movable limit, the limit detection sensor S11 is provided as a countermeasure against the displacement, due to an external factor or a failure. This prevents the movable part 3 from being moved outside a detection range of the limit detection sensor.

[Alignment Operation Member]

Figure 2:
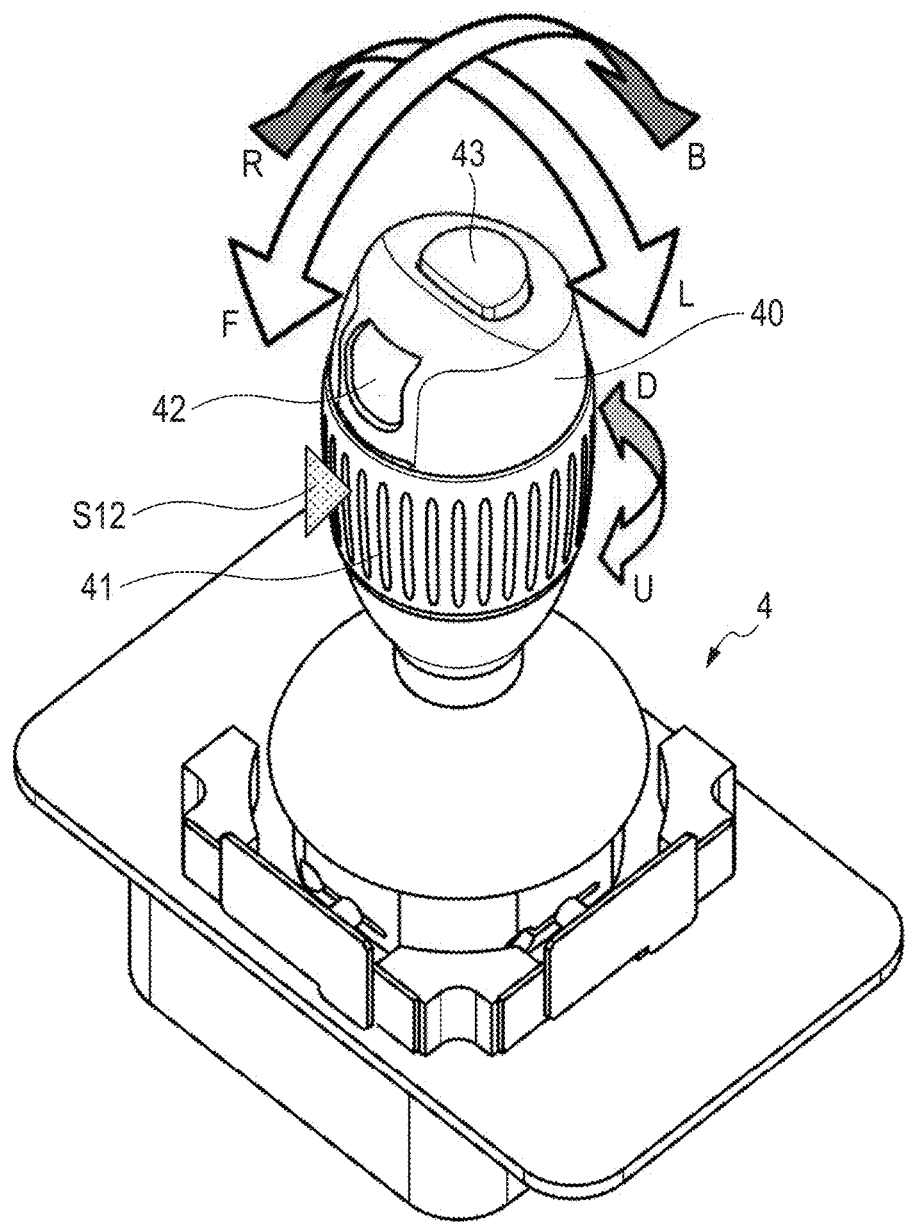
FIG. 2 is a perspective view of an alignment operation member of the fundus camera.

FIG. 2 is a perspective view of the alignment operation member of the fungus camera illustrated in FIG. 1A.

The alignment operation member 4 includes the following components for operating the above-mentioned slide mechanism and drive mechanism: an operation rod 40, a rotary dial 41, a Y alignment operation amount detection sensor S12, an anterior ocular segment/fundus switching switch 42, and a photographing switch 43.

The operation rod 40 is used as a holding member during a rough movement time during which the ophthalmic part 6 is roughly aligned with the eye E to be inspected so as to move the movable part 3 in the XZ-directions and is used as an inclining operation member during a fine movement time during which the alignment is finely made. When the inspector manually operates the operation rod 40, a not illustrated center ball coaxially provided below the operation rod 40 is slid on a not illustrated friction plate fitted to the fixing part 1, thereby allowing the movable part 3 to be roughly moved in the horizontal direction. Further, when the inspector inclines the operation rod 40 in the FB and LR directions, the not illustrated center ball rolls on the not illustrated friction plate without be slid, thereby allowing the movable part 3 to be finely moved in the horizontal direction.

The rotary dial 41 is used for rotary operation to move the ophthalmic part 6 in the Y-direction. The rotary dial 41 is disposed coaxially with the operation rod 40 and incorporates the Y alignment operation amount detection sensor S12. When the inspector rotates the rotary dial 41 in the UD direction, the Y alignment operation amount detection sensor S12 detects a rotation direction and a rotation angle per unit time. The system controller 100 drives the Y motor M3 in accordance with an operation amount rotary dial 41 to move the ophthalmic part 6 in the Y-direction. The anterior ocular segment/fundus switching switch 42 is a switch for changing over imaging elements to be described later for display on the display part 7. The photographing switch 43 is a switch for performing photographing.

[Focus Operation Member]

The focus operation member 5 includes a focus dial disposed coaxially with the alignment operation member 4 and a focus operation amount detection sensor S13 disposed inside the focus dial.

When the inspector rotates the focus dial, the focus operation amount detection sensor S13 detects a rotation direction and a rotation angle per unit time. The system controller 100 drives a focus lens drive motor to be described later in accordance with an operation amount of the focus dial to move a focus lens to be described later.

[Optical System]

Figure 3:
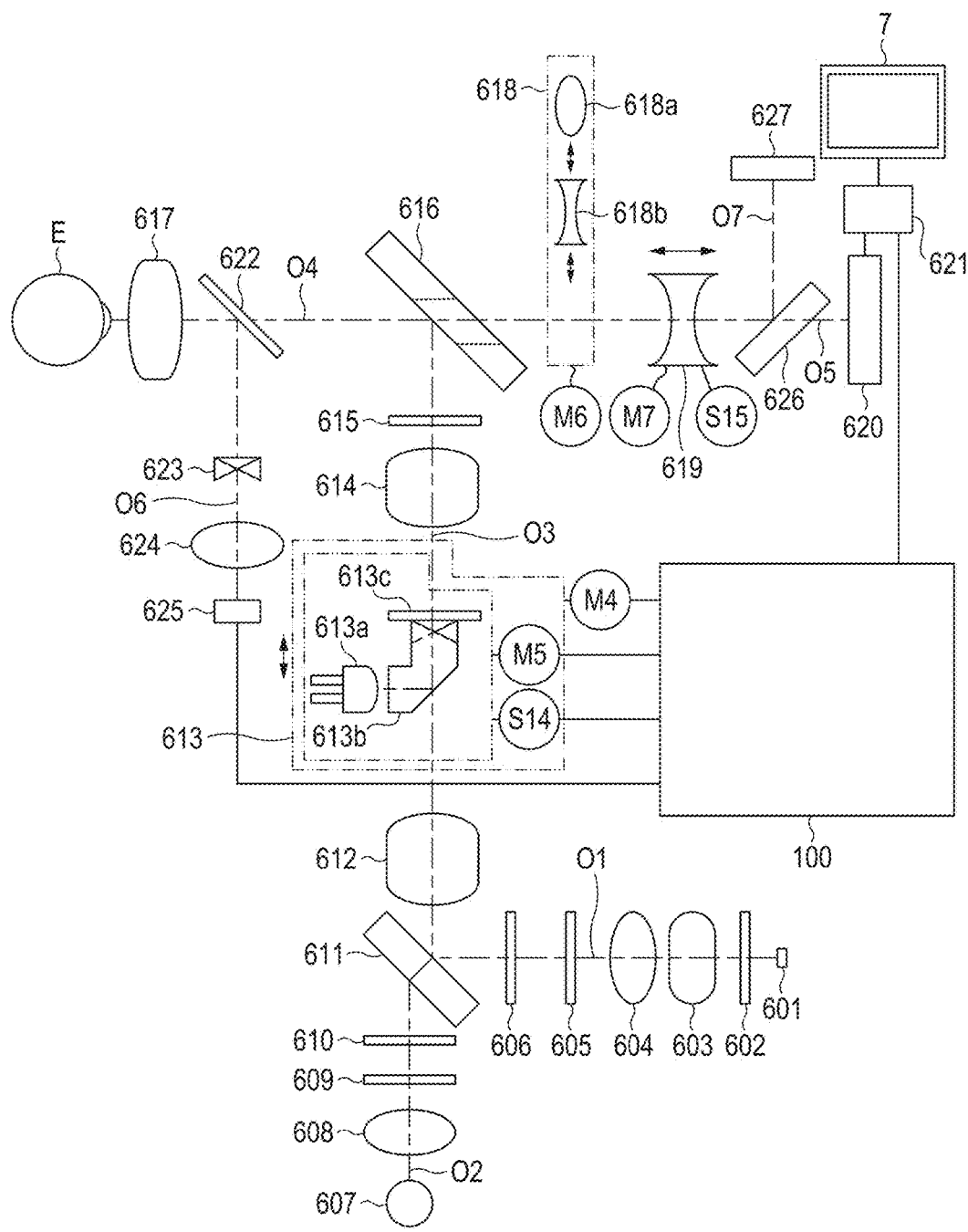
FIG. 3 is a view illustrating a configuration of an optical system of an ophthalmic part in the fundus camera.

FIG. 3 is a view illustrating a configuration of an optical system of the ophthalmic part in the fundus camera illustrated in FIG. 1A.

The optical system of the ophthalmic part 6 roughly includes a photographing light source part O1, an observation light source part O2, an illumination optical system O3, a photographing/illumination optical system O4, a photographing optical system O5, an anterior ocular segment observation optical system O6, and an internal fixation lamp part O7. A light beam emitted from the photographing light source part O1 or observation light source part O2 illuminates the eye E to be inspected through the illumination optical system O3 and photographing/illumination optical system O4. Thereafter, a part of an image of the eye E to be inspected is formed on an imaging element through the photographing/illumination optical system O4 and photographing optical system O5, and the other part thereof is formed on another imaging element through the anterior ocular segment observation optical system O6.

The photographing light source part O1 has the following configuration. A light amount detection unit 601 is a sensor, such as a photodiode (PD), that utilizes photoelectric conversion. A mirror 602 is formed of a glass plate deposited with aluminum or silver or formed of an aluminum plate. The mirror 602 transmits light near an optical axis and reflects light other than the light near the optical axis. A photographing light source 603 has structure in which Xe is encapsulated in a glass tube. When being applied with voltage, the photographing light source 603 emits light, whereby white light having an intensity sufficient to record a fundus image can be obtained at photographing time. A photographing condenser lens 604 is a general spherical lens. A photographing ring slit 605 is a flat plate having an annular opening. A photographing crystalline lens baffle 606 is also a flat plate having an annular opening. A part of a light beam emitted from the photographing light source 603 is directed in a direction toward the fundus and, further, a light beam emitted in an opposite direction is reflected by the mirror 602 to be directed in the direction toward the fundus. Thus, an emission amount of the photographing light source 603 can be reduced as compared to that in a configuration not including the mirror 602. A surface of the mirror 602 is made flat, so that unevenness of light does not occur, and there is no restriction on the photographing light source 603 in terms of distance. The light beam is then condensed toward the fundus by means of the photographing condenser lens 604 and is shaped by the photographing ring slit 605 such that a beam shape when the light beam passes through the anterior on segment is made annular. After that, a range of the light beams after shaping to be projected on a crystal lens of the eye to be inspected is limited by the photographing crystalline lens baffle 606 to prevent reflection of reflected light from a crystalline lens onto the fundus.

The observation light source part O2 has the following configuration. An observation light source 607 is a light source, such as an LED, capable of continuously emitting light and emits infrared light depending on element characteristics or a type of an optical filter. An observation condenser lens 608 is a general spherical lens. An observation ring slit 609 is a flat plate having an annular opening. An observation crystalline lens baffle 610 is also a flat plate having an annular opening. The above components are different from those in the photographing light source part O1 only in the type of the light source. In the observation light source part O2, the light beam is condensed by means of the observation condenser lens 608 and is shaped by the observation ring slit 609 such that a beam shape when the light beam passes through the anterior ocular segment is made annular. After that, a range of the light beams after shaping to be projected on a crystal lens of the eye to be inspected is limited by the observation crystalline lens baffle 610 to prevent reflection of reflected light from a crystalline lens onto the fundus.

The illumination optical system O3 relays the light beam created by the photographing light source part O1 and observation light source part O2 and forms an index image for focusing of the fundus image. A dichroic mirror 611 transmits an infrared light and reflects a visible light. The visible light beam created by the photographing light source part O1 reflected, while the infrared light beam created by the observation light source part O2 is transmitted to be led to the illumination optical system O3. A ring-shaped illumination light is focused on the eye E to be inspected by a first illumination relay lens 612 and a second illumination relay lens 614.

A split unit 613 has a focus index light source 613a, a prism 613b, a focus index mask 613c, an insert/retract mechanism to be described later, and a moving mechanism to be described later. The focus index light source 613a is used for projecting a focus index, and the prism 613b is used for splitting the light source. The focus index mask 613c is used for showing an outer shape of the focus index. The insert/retract mechanism has a split insert/retract drive motor M4. The split insert/retract drive motor M4 inserts the split unit 613 into the illumination optical system O3 at fundus observation time and projects split index in observation image. Further, at photographing time, the split insert/retract drive motor M4 retracts the split unit 613 from the illumination optical system O3 so as to prevent reflection of the focus index onto a photographing image. The moving mechanism has a split shift drive motor M5 and a split position sensor S14. The split shift drive motor M5 drives the focus index light source 613a, prism 613b, and focus index mask 613c to shift them in an optical axis direction (direction indicated by a double headed arrow in FIG. 3). By this shift drive of these components, the focus index is focused at fundus observation time, and stop positions of the components are detected by the split position sensor S14.

A cornea baffle 615 prevents reflection of unnecessary reflected light from a cornea of the eye E to be inspected onto the fundus image.

The photographing/illumination optical system O4 projects an illumination light beam onto the eye E to be inspected and derives a reflected light beam from the eye E to be inspected. A holed mirror 616 is a mirror having a hole at its center. A light beam led from the illumination optical system O3 is reflected by the mirror portion to illuminate the eye E to be inspected through an objective lens 617. A part of the reflected light beam from the illuminated eye E to be inspected returns to pass through the objective lens 617 and the hole at the center of the holed mirror 616 to be led to the photographing optical system O5.

The photographing optical system O5 adjusts focus of the fundus image of the eye E to be inspected and then forms the resultant fundus image on the imaging element. A diopter correction lens 618 includes a convex lens and a concave lens arranged so as to be insertable/retractable with respect to the photographing optical system O5 in order to focus the fundus of the eye E to be inspected in a case where the eye E to be inspected is so extremely long-sighted or short-sighted that focus adjustment cannot be made with a focus lens 619 to be described. When a patient is extremely short-sighted, a diopter correction minus lens 618b is inserted/retracted with respect to the photographing optical system O5 by a diopter correction lens insert/retract motor M6; while when the patient is extremely long-sighted, a diopter correction plus lens 618a is inserted/retracted with respect to the photographing optical system O5 by a diopter correction lens insert/retract motor M6.

The focus lens 619 is a lens for focus adjustment of a photographing light beam that has passed through the center hole of the holed mirror 616 and is moved in a direction indicated by a double headed arrow in FIG. 3 to thereby perform the focus adjustment. A focus lens drive motor M7 and a focus lens position sensor S15 drive the focus lens 619 to adjust the focus and detects a stop position of the focus lens 619. An imaging element 620 photoelectric-converts the photographing light. An electric signal obtained by the imaging element 620 is A-D converted into digital data by an image processing part 621. The resultant digital data is displayed on the display part 7 at time of observation of the infrared light and is recorded in a not illustrated recording medium after photographing.

In the anterior ocular segment observation optical system O6, a light path from the photographing/illumination optical system O4 is divided by a half mirror 622. The reflected light from the anterior ocular segment of the eye E to be inspected is partially reflected by the half mirror 622 and then passes through an anterior ocular segment prism 623 to be focused on an anterior ocular segment imaging element 625 having sensitivity of an infrared region by a lens 624. With the above optical systems, it is possible to observe the anterior ocular segment of the eye E to be inspected and to detect an alignment state between the eye E to be inspected and ophthalmic part 6.

In the an internal fixation lamp part O7, a light path from the photographing optical system O5 is divided by a half mirror 626, and an internal fixation lamp unit 627 faces the light path directed to the an internal fixation lamp part O7. The internal fixation lamp unit 627 is constituted by a plurality of LEDs and turns ON an LED corresponding to a fixation position selected by the inspector. A subject fixedly views the lighted LED and thereby the inspector can obtain a fundus image in a desired direction.

[Control System]

Figure 4:
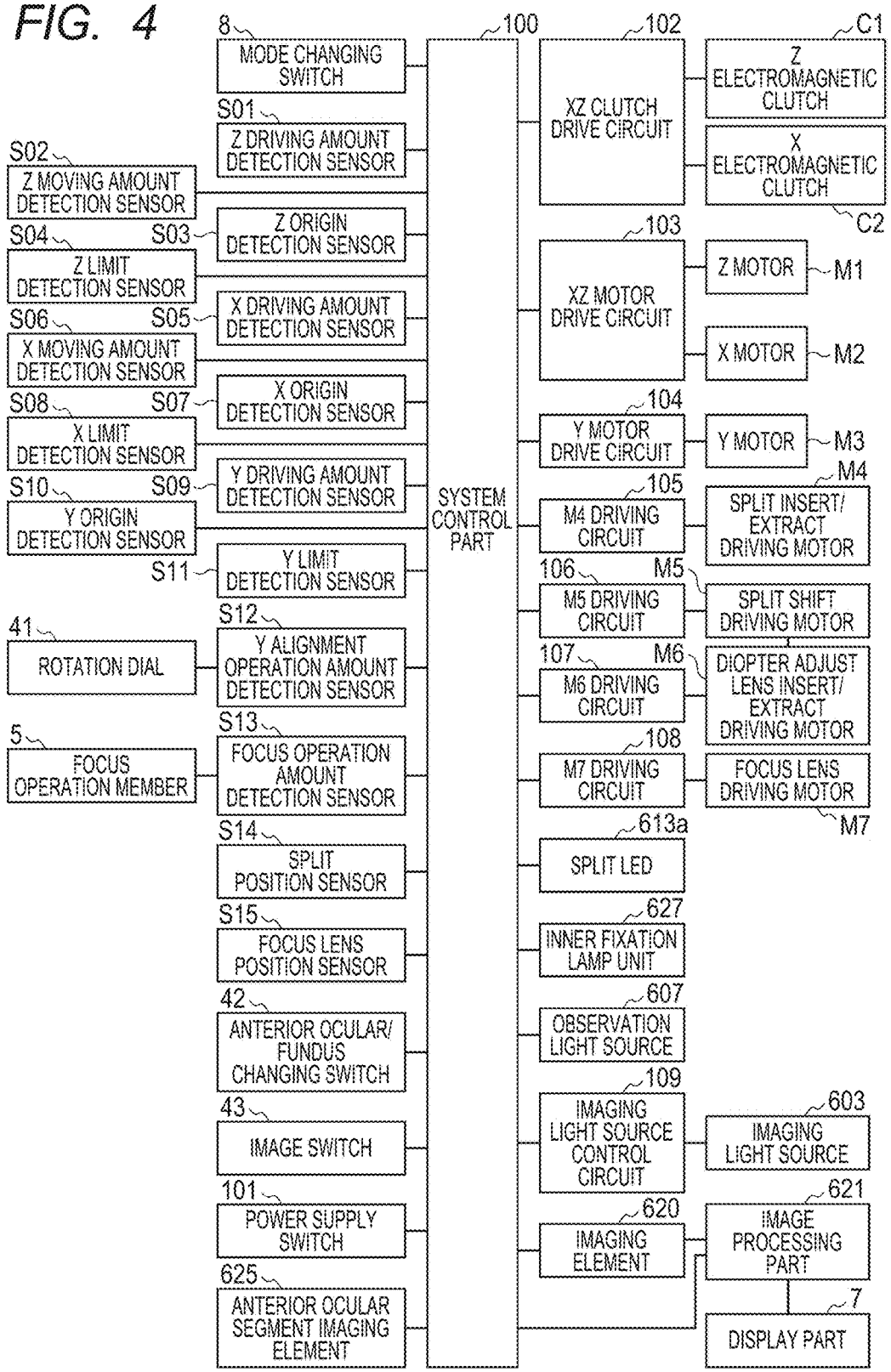
FIG. 4 is an electric block diagram of the fundus camera.

FIG. 4 is an electric block diagram of the fundus camera illustrated in FIGS. 1A and 1B.

All the following operations of the fundus camera are controlled by the system controller 100.

A power switch 101 is a switch for selecting a power supply state of the fundus camera.

An XZ clutch drive circuit 102 stops energization to the Z electromagnetic clutch C1 and X electromagnetic clutch C2 so as not to transmit drive force of the Z motor M1 and X motor M2 to the slide mechanism in the manual alignment mode; on the other hand, in the auto alignment mode, the XZ clutch drive circuit 102 energizes the Z electromagnetic clutch C1 and X electromagnetic clutch C2 so as to transmit drive force of the Z motor M1 and X motor M2 to the slide mechanism.

An XZ motor drive circuit 103 drives the Z motor M1 and Z motor M2 in accordance with outputs of the X and Z sensors S01 to S08 and an output of the system controller 100 with respect to an alignment state to be described later in a semi-auto mode and a full auto mode to be described later. A Y motor drive circuit 104 drives the Y motor M3 in accordance with outputs of the Y sensors S09 to S11 and an output of the Y alignment operation amount detection sensor S12 in a full manual mode to be described later; on the other hand, in the semi-auto mode and full auto mode to be described later, the Y motor drive circuit 104 drives the Y motor M3 in accordance with the outputs of the Y sensors S09 to S11 and output of the system controller 100 with respect to the alignment state to be described later.

An M4 drive circuit 105 drives the split insert/retract drive motor M4 so that the split unit 613 is retracted from the illumination optical system O3 when the photographing switch 43 is depressed by the inspector in the full manual mode or semi-auto mode to be described later. Further, in the full auto mode to be described later, the M4 drive circuit 105 drives the split insert/retract drive motor M4 so that the split unit 613 is retracted from the illumination optical system O3 when all photographing conditions are met to allow auto shot to be performed. An M5 drive circuit 106 drives the split shift drive motor M5 in accordance with outputs of the focus sensors S13 to S15 in the full manual mode to be described later. Further, the M5 drive circuit 106 drives the split shift drive motor M5 in accordance with outputs of the focus sensors S14 and S15 and output of the system controller 100 with respect to a focus state to be described later in the semi-auto mode or full auto mode to be described later.

An M6 drive circuit 107 drives the diopter correction lens insert/retract motor M6 in accordance with the outputs of the focus sensors S13 to S15 in the full manual mode to be described later. Further, the M6 drive circuit 107 drives the diopter correction lens insert/retract motor M6 in accordance with the outputs of the focus sensors S14 and S15 and output of the system controller 100 with respect to the focus state to be described later in the semi-auto mode or full auto mode to be described later.

An M7 drive circuit 108 drives the focus lens drive motor M7 in accordance with the outputs of the focus sensors S13 to S15 in the full manual mode to be described later. Further, the M7 drive circuit 108 drives the focus lens drive motor M7 in accordance with the outputs of the focus sensors S14 and S15 and output of the system controller 100 with respect to the focus state to be described later in the semi-auto mode or full auto mode to be described later.

A photographing light source control circuit 109 charges energy for emitting a photographing light source 603 before photographing and discharges the charged electric energy at photographing time to thereby emit the photographing light source 603.

[Alignment Principle/Index]

Figure 5A:
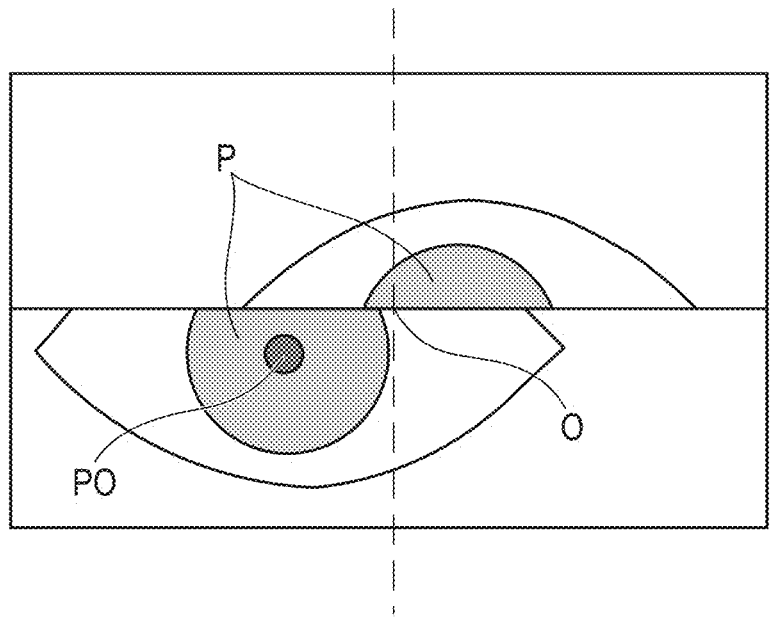
FIGS. 5A and 5B are schematic views explaining a principle of alignment using a prism of the fundus camera.
Figure 5B:
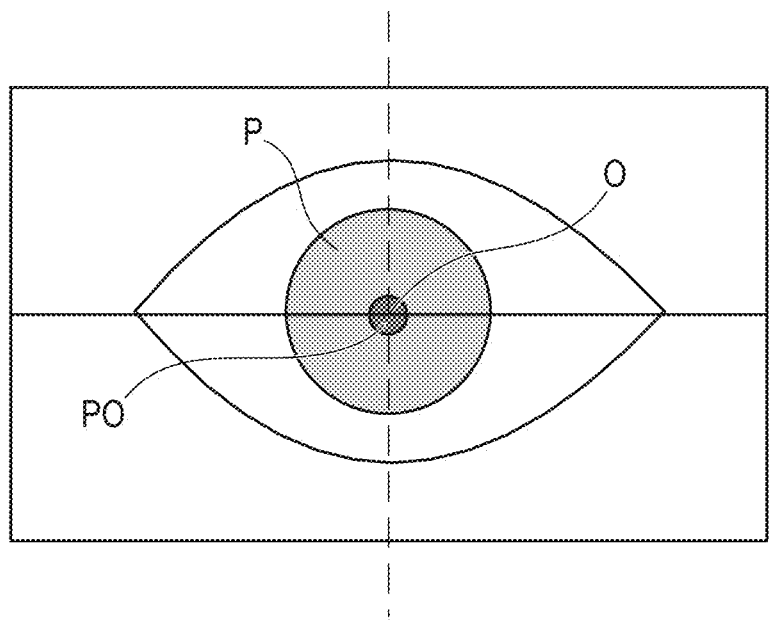

FIGS. 5A and 5B are schematic views explaining a principle of alignment using a prism of the fundus camera.

More specifically, FIGS. 5A and 5B each illustrate an observation image on the imaging element 625 of the anterior ocular segment observation optical system O6 described using FIG. 3. The eye E to be inspected is divided up and down by the anterior ocular segment prism 623 and is observed on the anterior ocular segment imaging element 625 as illustrated in FIG. 5A. Alignment with respect to the eye E to be inspected in the forward-backward direction is performed according to the following principle. Light incident on the anterior ocular segment prism 623 are separated into upper and lower halves which are refracted in opposite (left and right) directions. Thus, in a case where a distance between the eye E to be inspected and ophthalmic part 6 is larger than a predetermined operation distance, an imaging position set by the lens 624 is shifted rightward at the upper half of the observation image and shifted leftward at the lower half thereof; on the other hand, in a case where distance between the eye P to be inspected and ophthalmic part 6 is smaller than a predetermined operation distance, an imaging position set by the lens 624 is shifted leftward at the upper half of the observation image and shifted rightward at the lower half thereof. Thus, the alignment in the forward-backward direction can be made by adjusting the shift direction of the observation direction.

Alignment with respect to the eye E to be inspected in the up-down and left-right directions is performed according to the following principle. A part of the eye E to be inspected other than the pupil has many reflected lights and thus appears white; on the other hand, a pupil portion P does not have reflected light and thus appears black. Thus, the pupil portion P can be extracted based on the contrast difference, allowing a pupil position to be determined. In FIG. 5A, in which the pupil portion P is divided into upper and lower parts, a pupil center P0 is detected from the pupil portion P of the lower part. As illustrated in FIG. 5B, by making the pupil center P0 coincide with an image center O of the anterior ocular segment imaging element 625, alignment between the eye E to be inspected and ophthalmic part 6 is made. In an anterior ocular segment manual alignment of the full manual mode to be described later included in the manual alignment mode, the inspector manually operates the alignment operation member 4 to perform the positioning. On the other hand, in the full auto mode and semi-auto mode to be described later included in the auto alignment mode, the positioning is automatically performed by the system controller 100. The optical system involved in the above alignment and a module region of the system controller 100 that performs the alignment (relative positioning) between the eye E to be inspected and ophthalmic part 6 constitute an alignment detection unit of the present embodiment.

Figure 6A:
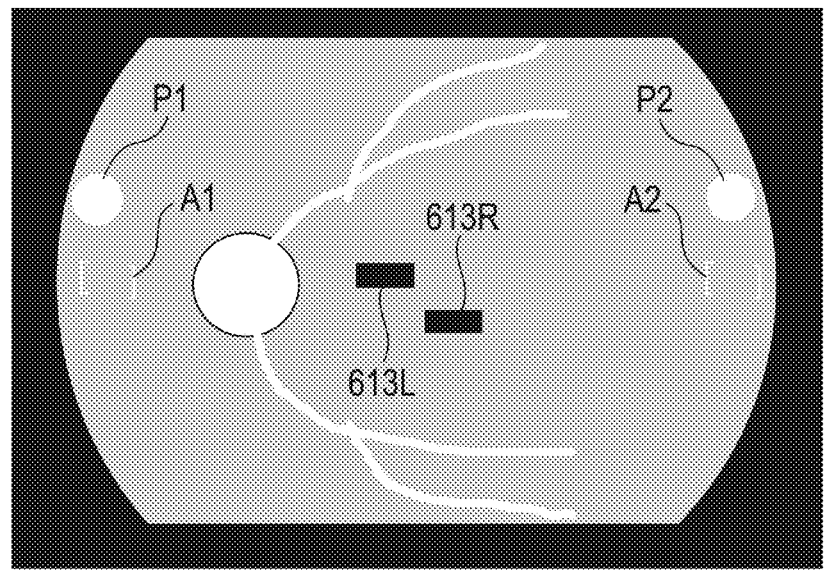
FIGS. 6A and 6B are schematic views explaining an alignment index and a focus index of a fundus observation image in the fundus camera.
Figure 6B:
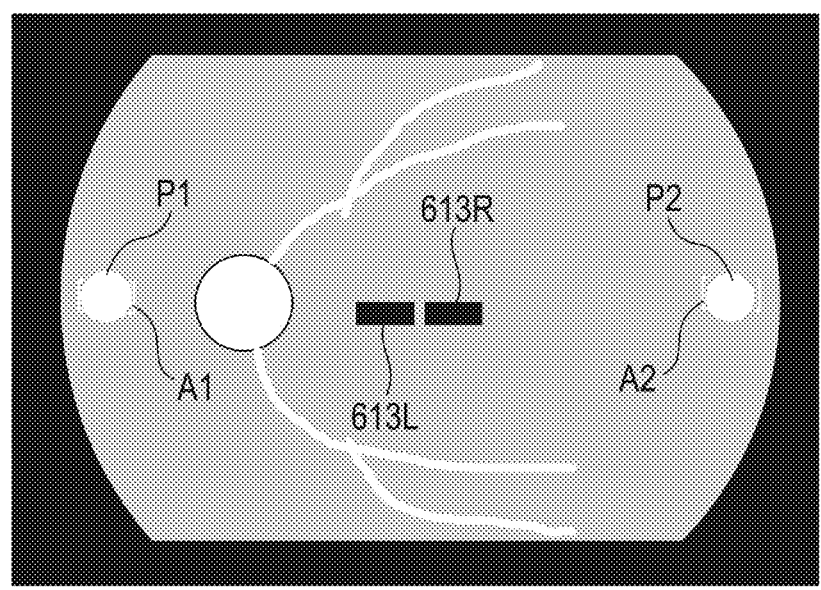

FIGS. 6A and 6B are schematic views explaining an alignment index and a focus index of a fundus observation image in the fundus camera. The focus index will be described later.

FIGS. 6A and 6B each illustrate a fundus observation image on the imaging element 620. An alignment index P1 and an alignment index P2 are two digital alignment indices symmetrically shifted from the photographing optical axis. A guide frame A1 and a guide frame A2 indicate alignment positions of the alignment index P1 and alignment index P2, respectively. In a fundus manual alignment of the full manual mode to be described later included in the manual alignment mode, the inspector manually operates the alignment operation member 4 to make the alignment indices P1 and P2 coincide with the guide frames A1 and A2, respectively. With this operation, the pupil center P0 of the eye E to be inspected detected according to the above alignment principle and image center O of the anterior ocular segment imaging element 625 coincide with each other, and the alignment between the eye E to be inspected and ophthalmic part 6 is achieved.

[Focus Principle/Index]

A focus index 613L and a focus index 613R are indices projected by the split unit 613 and split on the eye E to be inspected. The split unit 613 and focus lens 619 are moved in conjunction with each other and control of the system controller 100, and the imaging element 620 and focus index mask 613c are substantially conjugate with each other optically. Thus, when the split unit 613 is shifted in the optical axis direction, split indices 613L and 613R are moved in the fundus observation image on the imaging element 620 and, in conjunction with this, the focus lens 619 is moved in the optical axis direction. That is, by bringing an arrangement state of the split indices 613L and 613R or the imaging element 620 from a state of FIG. 6A to a state of FIG. 6B (aligned state), focus is adjusted on the fundus of the eye E to be inspected.

In the full manual mode to be described later, the inspector manually operates the focus operation member 5 to perform the above index alignment. On the other hand, in the full auto mode and semi-auto mode to be described later where auto focus is performed, the index alignment is automatically performed by the system controller 100.

[Flowchart]

Figure 7:
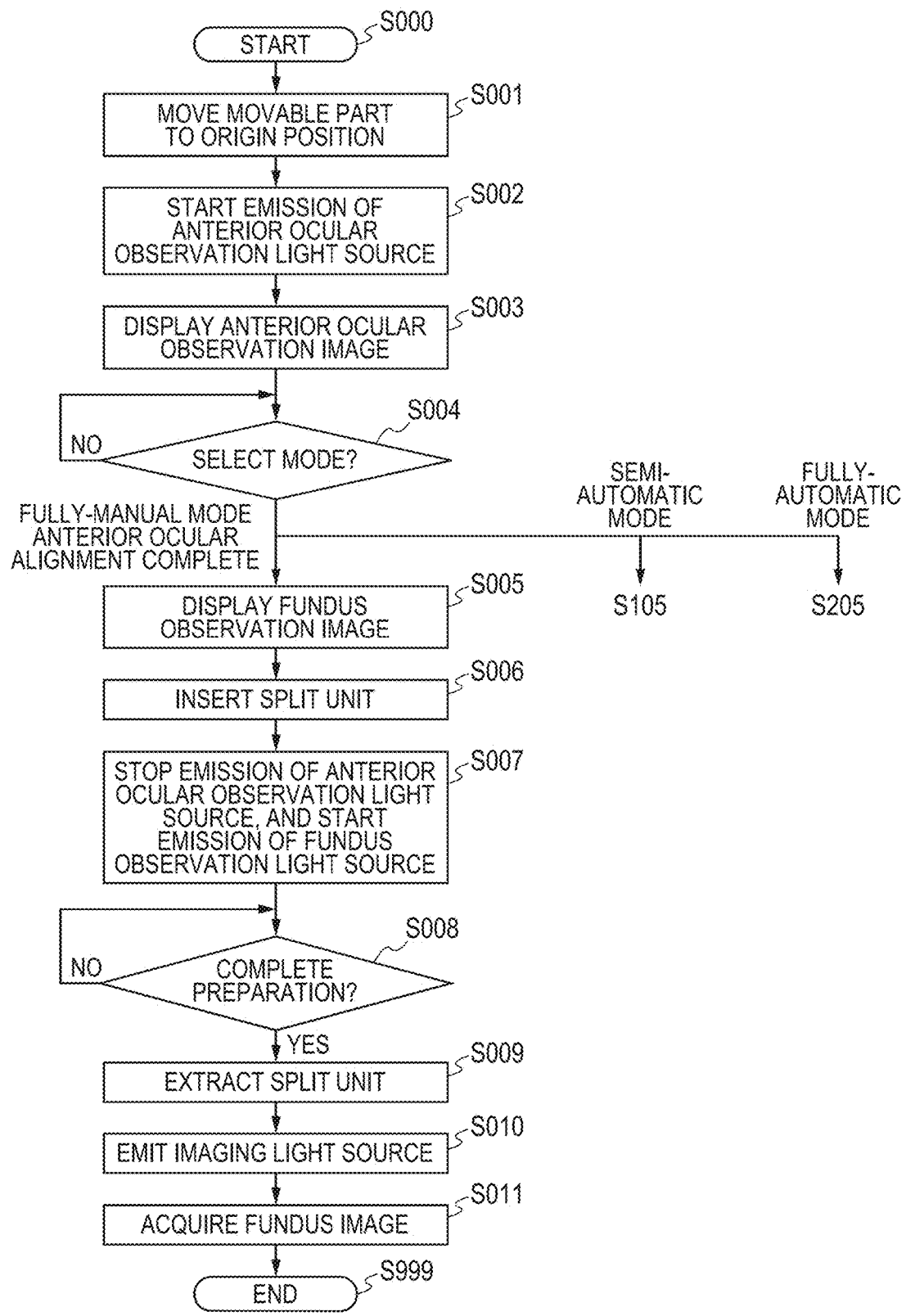
FIG. 7 is a flowchart illustrating an operation procedure in the full manual mode in a fundus camera photographing sequence.

FIG. 7 is a flowchart illustrating an operation procedure in the full manual mode in a fundus camera photographing sequence.

In (S000), the photographing sequence is started.

In (S001), the movable part 3 is moved to a reference position. Completion of the movement of the movable part 3 to the reference position is detected by outputs of the Z reference detection sensor S03, X reference detection sensor S07, and Y reference detection sensor S10, and the procedure proceeds to (S002).

In (S002), emission of a not illustrated anterior ocular segment observation light source is started.

In (S003), an image on the anterior ocular segment imaging element 625 is displayed on the display part 7.

In (S004), one of the full manual mode, semi-auto mode, full auto mode is selected. The photographing mode is switched in above order every time the mode switching switch 8 is depressed. A mode currently being selected is displayed on the display part 7. In the full manual mode, it is determined whether or not the anterior ocular segment alignment between the ophthalmic part 6 and eye E to be inspected is completed.

After completion of the photographing sequence, or after activation of the fundus camera, the full manual mode is selected. The inspector manually operates the alignment operation member 4 to perform the anterior ocular segment alignment and depresses the anterior ocular segment/fundus switching switch 42 after completion of the alignment. When depression of anterior ocular segment/fundus switching switch 42 is detected in a state where the photographing mode is not switched to the semi-auto mode or full auto mode, selection of the full manual mode is determined, and completion of the anterior ocular segment alignment is determined. Then, the procedure proceeds to (S005). Depending on the setting, the anterior ocular segment/fundus switching may be automatically performed based on detection of completion the anterior ocular segment alignment. In this case, selection of the full manual mode is determined based on the anterior ocular segment/fundus switching.

When the photographing mode is switched to the semi-auto mode, the procedure proceeds to (S105). When the photographing mode is switched to the full auto mode, the procedure proceeds to (S205). When the anterior ocular segment/fundus switching switch 42 is not depressed, it is determined that the photographing models being selected or the anterior ocular segment alignment is being performed, and a waiting state is maintained until depression of the anterior ocular segment/fundus switching switch 42.

First, a photographing sequence in the full manual mode will be described.

In (S005), the image on the imaging element 620 is displayed on the display part 7.

In (S006), the split insert/retract drive motor M4 is driven to insert the split unit 613 into the illumination optical system O3.

In (S007), emission of the not illustrated anterior ocular segment observation light source is stopped, and emission of a fundus observation light source 607 is started.

In (S008), it is determined whether or not photographing preparation is completed. The inspector manually operates the alignment operation member 4 to perform fundus alignment and manually operates the focus operation member 5 to perform focusing of the fundus image. After completion of the fundus alignment and focusing of the fundus image, the inspector depresses the photographing switch 43. When the depression of the photographing switch 43 is detected, it is determined that the photographing preparation is completed, and the procedure proceeds to (S009). When the photographing switch is not depressed, it is determined that the photographing preparation is being made, and a waiting state is maintained until the depression of the photographing switch 43. Depending on the setting, auto focus and auto shot may be selected and performed.

In (S009), the split insert/retract drive motor M4 is driven to retract the split unit 613 from the illumination optical system O3.

In (S010), the photographing light source 603 emits light to irradiate the fundus of the eye E to be inspected with a visible light.

In (S011), the fundus image is photographed.

In (S999), the photographing sequence in the full manual mode is completed.

A photographing sequence in the semi-auto mode will next be descried.

Figure 8:
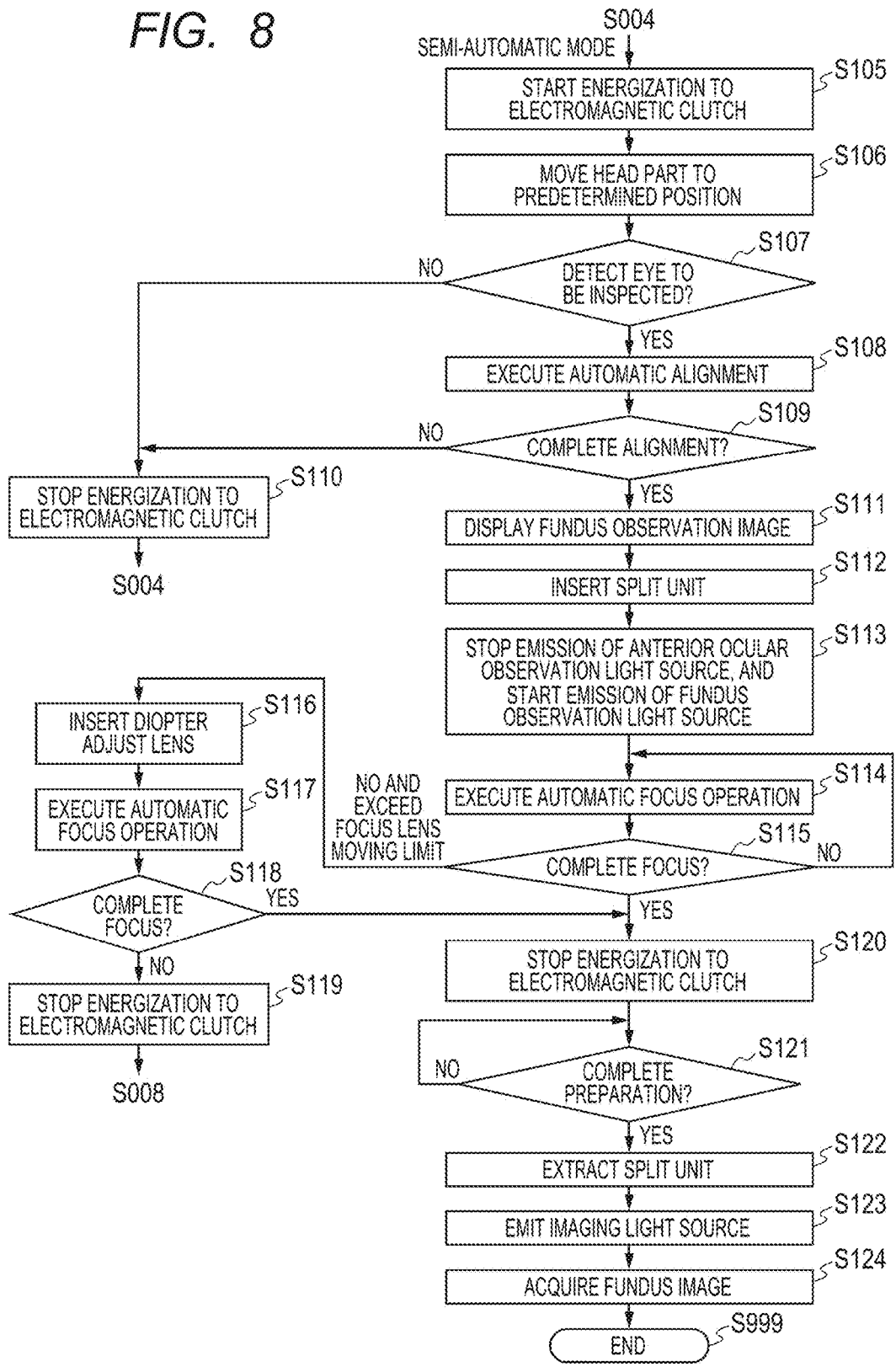
FIG. 8 is a flowchart illustrating an operation procedure in the semi-auto mode in the fundus camera photographing sequence.

FIG. 8 is a flowchart illustrating an operation procedure in the semi-auto mode in the fundus camera photographing sequence.

In (S105), the Z electromagnetic clutch C1 and X electromagnetic clutch C2 are energized to allow the drive force from the drive parts D1 and D2 to be transmitted to the slide mechanism. In the present embodiment, the procedure proceeds to (S106) after waiting of 30 msec as an interval, from the energization to the electromagnetic clutches C1 and C2 to completion of connection. An "electromagnetic clutch energization start" sequence to be described hereinafter has the same interval.

In (S106), the Z motor M1, X motor M2, and Y motor M3 are driven to move the ophthalmic part 6 to a predetermined position for detection of the eye E to be inspected.

In (S107), detection determination of the eye E to be inspected is made. When the eye E to be inspected is detected from the anterior ocular segment observation image, the procedure proceeds to (S108). When the eye E to be inspected cannot be detected, the procedure proceeds to (S110).

In (S108), the Z motor M1, X motor M2, and Y motor M3 are driven to perform auto alignment.

In (S109), auto alignment completion determination is made. When a displacement amount between the pupil center P0 of the eye E to be inspected and image center O of the anterior ocular segment imaging element 625 is less than a prescribed amount, it is determined that the auto alignment is completed, and the procedure proceeds to (S111). On the other hand, when the displacement amount is equal to or more than the prescribed amount, it is determined that the auto alignment cannot be made, and the procedure proceeds to (S110).

In (S110), energization to the Z electromagnetic clutch C1 and X electromagnetic clutch C2 is stopped to prevent the drive force from the drive parts D1 and D2 from being transmitted to the slide mechanism, and the photographing mode shifts to the full manual mode. After that, the procedure proceeds to (S004). In the present embodiment, information designating that the photographing mode has shifted to the full manual mode is displayed or the display part 7 after waiting of about 50 msec as an interval between the stop of energization to the electromagnetic clutches C1 and C2 to release of the connection, and the procedure proceeds to (S004). An "electromagnetic clutch energization stop" sequence to be described hereinafter has the same interval.

In (S111), the image on the imaging element 620 is displayed on the display part 7.

In (S112), the split insert/retract drive motor M4 is driven to insert the split unit 613 into the illumination optical system O3.

In (S113), emission of the not illustrated anterior ocular segment observation light source is stopped, and emission of the fundus observation light source 607 is started.

In (S114), the split shift drive motor M5 and focus lens drive motor M7 are driven in conjunction with each other to perform auto focus.

In (S115), auto focus completion determination is made. When a displacement amount between the focus split indices 613L and 613R is equal to or less than a prescribed amount, it is determined that the auto focus is completed, and the procedure proceeds to (S120). On the other hand, in a case where the displacement amount is more than the prescribed amount and where an output of the focus lens position sensor S14 does not indicate a focus lens movable range end, the procedure returns to (S114). In a case where the displacement amount is more than the prescribed amount and where the output of the focus lens position sensor 614 indicates a focus lens movable range end, the procedure proceeds to (S116).

In (S116), the diopter correction lens insert/retract motor M6 is driven to insert the diopter correction lens 618 into the photographing optical system.

In (S117), in a state where the diopter correction lens 618 is inserted into the photographing optical system O5, the split shift drive motor M5 and focus lens drive motor M7 are driven in conjunction with each other to perform auto focus.

In (S118), auto focus completion determination is made. When a displacement amount between the focus split indices 613L and 613R is equal to or less than a prescribed amount, it is determined that the auto focus is completed, and the procedure proceeds to (S120). On the other hand, when the displacement amount is more than the prescribed amount, it is determined that the auto focus cannot be made, and the procedure proceeds to (S119).

In (S119), energization to the Z electromagnetic clutch C1 and X electromagnetic clutch C2 is stopped to prevent the drive force from the drive parts D1 and D2 from being transmitted to the slide mechanism, and the photographing mode shifts to the full manual mode. After that, the procedure proceeds to (S008).

In (S120), energization to the Z electromagnetic clutch C1 and X electromagnetic clutch C2 is stopped to prevent the drive force from the drive parts D1 and D2 from being transmitted to the slide mechanism, and the photographing mode shifts to the manual alignment mode.

In (S121), it is determined whether or not photographing preparation is completed. The inspector manually operates the alignment operation member 4 to perform fundus alignment and manually operates the focus operation member 5 to perform focusing of the fundus image. After completion of the fundus alignment and focusing of the fundus image, the inspector depresses the photographing switch 43. When the depression of the photographing switch 43 is detected, it is determined that the photographing preparation is completed, and the procedure proceeds to (S122). When the photographing switch is not depressed, it is determined that the photographing preparation is being made, and a waiting state is maintained until the depression of the photographing switch 43.

In (S122), the split insert/retract drive motor M4 is driven to retract the split unit 613 from the illumination optical system O3.

In (S123), the photographing light source 603 emits light to irradiate the fundus of the eye E to be inspected with a visible light.

In (S124), the fundus image is photographed.

In (S999), the photographing sequence in the semi-auto mode is completed.

A photographing sequence in the full auto mode will next be descried.

Figure 9:
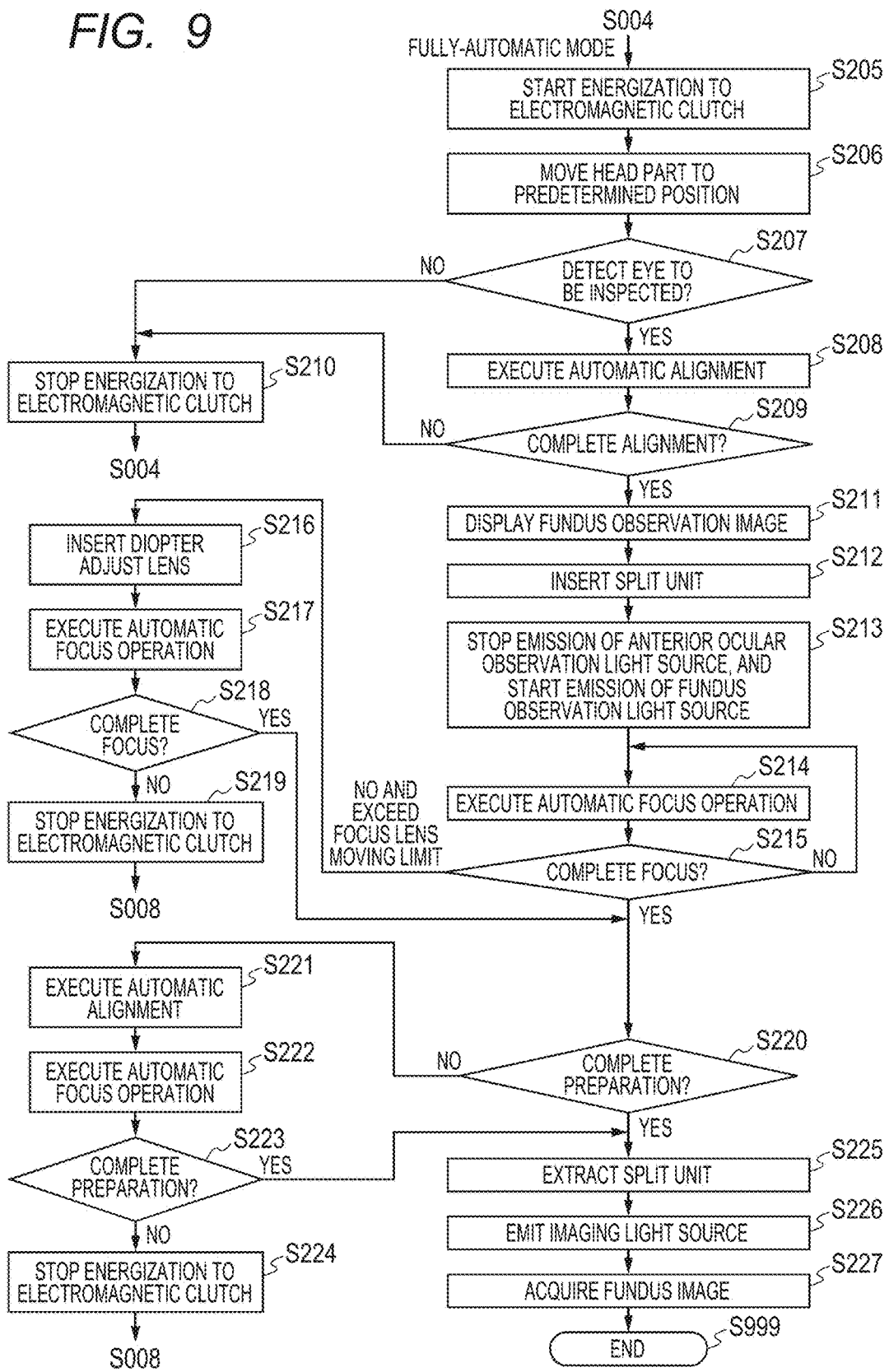
FIG. 9 is a flowchart illustrating an operation procedure in the full auto mode in the fundus camera photographing sequence.

FIG. 9 is a flowchart illustrating an operation procedure in the full auto mode in the fundus camera photographing sequence.

In (S205), the Z electromagnetic clutch C1 and X electromagnetic clutch C2 are energized to allow the drive force from the drive parts D1 and D2 to be transmitted to the slide mechanism.

In (S206), the Z motor M1, X motor M2, and Y motor M3 are driven to move the ophthalmic part 6 to a predetermined position for detection of the eye E to be inspected.

In (S207), detection determination of the eye E to be inspected is made. When the eye E to be inspected is detected from the anterior ocular segment observation image, the procedure proceeds to (S208). When the eye E to be inspected cannot be detected, the procedure proceeds to (S210).

In (S208), the Z motor M1, X motor M2, and Y motor M3 are driven to perform auto alignment.

In (S209), auto alignment completion determination is made. When a displacement amount between the pupil center P0 of the eye E to be inspected and image center O of the anterior ocular segment imaging element 625 is less than a prescribed amount, the procedure proceeds to (S211). On the other hand, when the displacement amount is equal to or more than the prescribed amount, it is determined that the auto alignment cannot be made, and the procedure proceeds to (S210). The displacement amount is example of a value designating a detected relative position, and the value used for the determination is not limited to the displacement amount as long as it indicates the relative position in like manner. Further, the prescribed amount to be compared with the displacement amount is grasped as a threshold value to be compared with a value designating the relative position. Determination of whether or not the detected value designating the relative position is equal to or more than the threshold value is executed by a module in the system controller 100 that functions as a determination unit.

In (S210), energization to the Z electromagnetic clutch C1 and X electromagnetic clutch C2 is stopped to prevent the drive force from the drive parts D1 and D2 from being transmitted to the slide mechanism, and the photographing mode shifts to the full manual mode. After that, the procedure proceeds to (S004). That is, when it is determined that the value designating the relative position is equal to or more than the threshold value, the system controller 100 controls the drive force transmit switching unit to stop transmission of the electric drive force to the movable unit to stop movement of the movable unit.

In (S211), the image on the imaging element 620 is displayed on the display part 7. Hereinafter, as described above, when the value designating the relative position is less than the threshold value, the controller executes the following operation procedures to control the drive force transmit switching unit to transmit the electric drive force to the movable unit to continue movement of the movable unit.

In (S212), the split insert/retract drive motor is driven to insert the split unit 613 into the illumination optical system O3.

In (S213), emission of the not illustrated anterior ocular segment observation light source is stopped, and emission of the fundus observation light source 607 is started.

In (S214), the split shift drive motor M5 and focus lens drive motor M7 are driven in conjunction with each other to perform auto focus.

In (S215), auto focus completion determination is made. When a displacement amount between the focus split indices 613L and 613R is equal to or less than a prescribed amount, i.e., focus threshold value, the procedure proceeds to (S220). On the other hand, in a case where the displacement amount is more than the prescribed amount (focus threshold value) and where an output of the focus lens position sensor S14 does not indicate a focus lens movable range end, the procedure returns to (S214). In a case where the displacement amount is more than the prescribed amount and where the output of the focus lens position sensor S14 indicates a focus lens movable range end, the procedure proceeds to (S216). Comparison determination between the displacement amount and focus threshold value is executed by a module in the system controller 100 that functions as a focus determination unit.

In (S216), the diopter correction lens insert/retract motor M6 is driven to insert the diopter correction lens 618 into the photographing optical system O5.

In (S217), in a state where the diopter correction lens 618 is inserted into the photographing optical system O5, the split shift drive motor M5 and focus lens drive motor M7 are driven in conjunction with each other to perform auto focus.

In (S218), auto focus completion determination is made. When a displacement amount between the focus split indices 613L and 613R is equal to or less than a prescribed amount, the procedure proceeds to (S220). On the other hand, when the displacement amount is more than the prescribed amount, the procedure proceeds to (S219).

In (S219), energization to the Z electromagnetic clutch C1 and X electromagnetic clutch C2 is stopped to prevent the drive force from the drive parts D1 and D2 from being transmitted to the slide mechanism, and the photographing mode shifts to the full manual mode. After that, the procedure proceeds to (S008).

In (S220), it is determined whether or not photographing preparation is completed. Further, the alignment completion determination is made once again. When a displacement amount between the pupil center P0 of the eye E to be inspected and image center O of the anterior ocular segment imaging element 625 is less than a prescribed amount, the procedure proceeds to (S225). On the other hand, when the displacement amount is equal to or more than the prescribed amount, the procedure proceeds to (S221).

In (S221), the Z motor M1, X motor M2, and Y motor M3 are driven to perform auto alignment once again.

In (S222), the split shift drive motor M5 and focus lens drive motor M7 are driven in conjunction with each other to perform auto focus.

In (S223), it is determined once again whether or not photographing preparation is completed. Then, the alignment completion determination and focus completion determination are made. When a displacement amount between the pupil center P0 of the eye E to be inspected and image center O of the anterior ocular segment imaging element 625 and a displacement amount between the focus split indices 613L and 613R are both equal to or less than prescribed amounts, respectively, the procedure proceeds to (S225). When one of the above displacement amounts is more than the prescribed amount, the procedure proceeds to (S224).

In (S224), energization to the Z electromagnetic clutch C1 and X electromagnetic clutch C2 is stopped to prevent the drive force from the drive parts D1 and D2 from being transmitted to the slide mechanism, and the photographing mode shifts to the full manual mode. After that the procedure proceeds to (S008).

In (S225), the split insert/retract drive motor M4 is driven to retract the split unit 613 from the illumination optical system O3.

In (S226), the photographing light source 603 emits light to irradiate the fundus of the eye E to be inspected with a visible light.

In (S227), the fundus image is photographed.

In (S999), the photographing sequence in the full auto mode is completed.

The photographing mode currently being selected is displayed on the display part 7.

In the above description related to the respective photographing modes, a sequence where the photographing mode shifts from the semi-auto mode and full auto mode to the full manual mode due to failure of the auto operation has been described. The following describes a sequence where the inspector depresses the mode switching switch 8 during execution of each photographing mode to switch the photographing mode.

Figure 10:
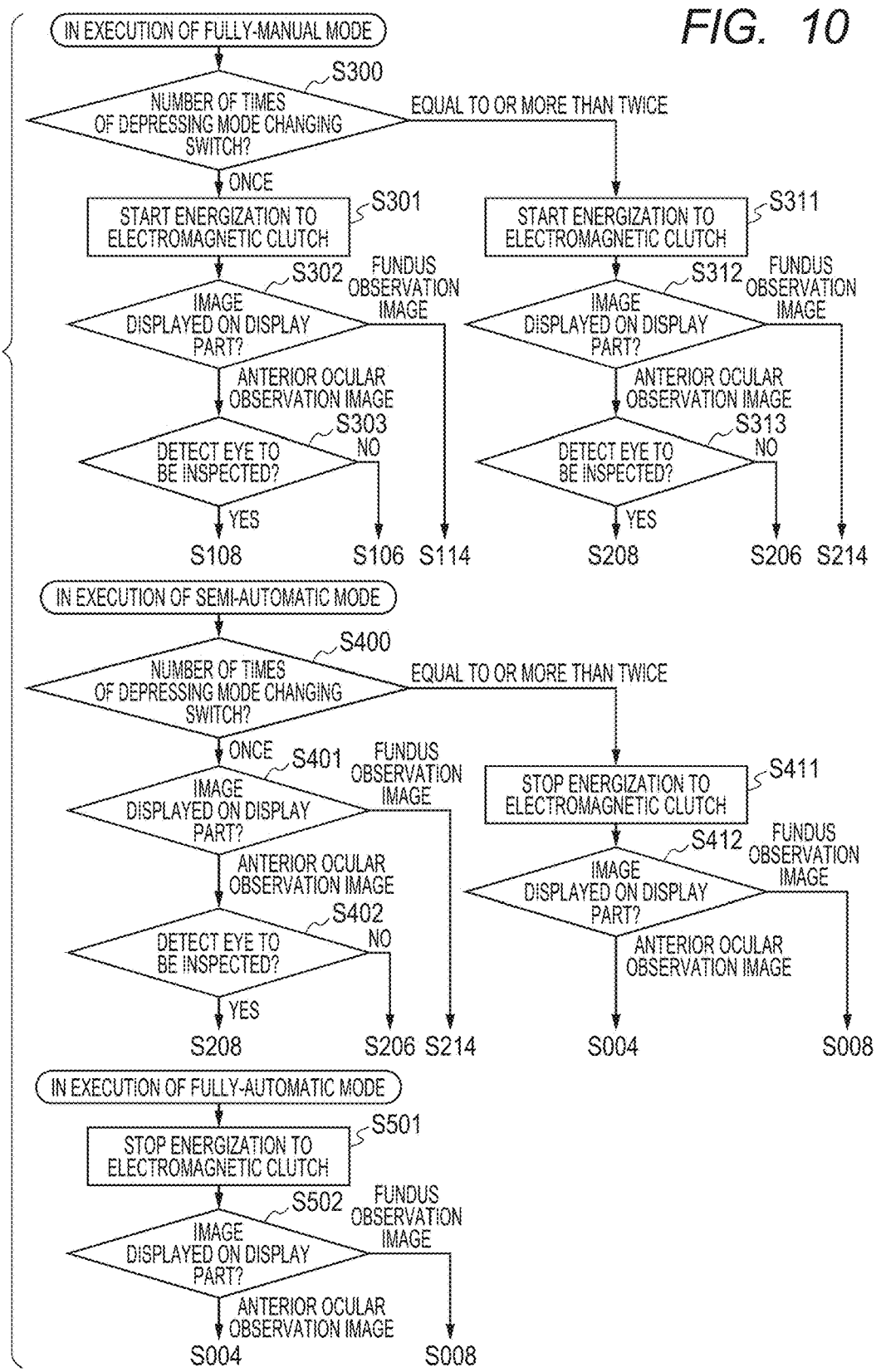
FIG. 10 is a flowchart illustrating an operation procedure concerning mode switching in the fundus camera photographing sequence.

FIG. 10 is a flowchart illustrating an operation procedure concerning mode switching in the fundus camera photographing sequence.

First, a case where the mode switching switch 8 is depressed during execution of the full manual mode will be described.

In (S300), the number of times of times that the mode switching switch 8 is continuously depressed during execution of the full manual mode is counted. When the mode switching switch 8 is depressed only once, the procedure proceeds to (S301). When the mode switching switch 8 is depressed twice or more, the procedure proceeds to (S311).

In (S301), the Z electromagnetic clutch C1 and X electromagnetic clutch C2 are energized to allow the drive force from the drive parts D1 and D2 to be transmitted to the slide mechanism.

In (S302), it is determined which of the anterior ocular segment observation image and fundus observation image is being displayed on the display part 7. When the image on the anterior ocular segment imaging element 625 is being displayed, the procedure proceeds to (S303). When the image on the imaging element 620 is being displayed, the photographing mode shifts to the semi-auto mode, and the procedure proceeds to (S114).

In (S303), detection determination of the eye E to be inspected is made. When the eye E to be inspected is detected from the anterior ocular segment observation image, the photographing mode shifts to the semi-auto mode, and the procedure proceeds to (S108). When the eye E to be inspected is not detected, the photographing mode shifts to the semi-auto mode, and the procedure proceeds to (S106).

In (S311), the Z electromagnetic clutch C1 and X electromagnetic clutch C2 are energized to allow the drive force from the drive parts D1 and D2 to be transmitted to the slide mechanism.

In (S312), it is determined which of the anterior ocular segment observation image and fundus observation image is being displayed on the display part 7. When the image on the imaging element 625 is being displayed, the procedure proceeds to (S313). When the image on the imaging element 620 is being displayed, the photographing mode shifts to the full auto mode, and the procedure proceeds to (S214).

In (S313), detection determination of the eye E to be inspected is made. When the eye E to be inspected is detected from the anterior ocular segment observation image, the photographing mode shifts to the full auto mode, and the procedure proceeds to (S208). When the eye E to be inspected is not detected, the photographing mode shifts to the full auto mode, and the procedure proceeds to (S206).

Next, a case where the mode switching switch 8 is depressed during execution of the semi-auto mode will be described.

In (S400), the number of times that the mode switching switch 8 is continuously depressed during execution of the semi-auto mode is counted. When the mode switching switch 8 is depressed only once, the procedure proceeds to (S401). When the mode switching switch 8 is depressed twice or more, the procedure proceeds to (S411).

In (S401), it is determined which of the anterior ocular segment observation image and fundus observation image is being displayed on the display part 7. When the image on the imaging element 625 is being displayed, the procedure proceeds to (S402). When the image on the imaging element 620 is being displayed, the photographing mode shifts to the full auto mode, and the procedure proceeds to (S214).

In (S402), detection determination of the eye E to be inspected is made. When the eye E to be inspected is detected from the anterior ocular segment observation image, the photographing mode shifts to the full auto mode, and the procedure proceeds to (S208). When the eye E to be inspected is not detected, the photographing mode shifts to the full auto mode, and the procedure proceeds to (S206).

In (S411), energization to the Z electromagnetic clutch C1 and X electromagnetic clutch C2 is stopped to prevent the drive force from the drive parts D1 and D2 from being transmitted to the slide mechanism.

In (S412), it is determined which of the anterior ocular segment observation image and fundus observation image is being displayed on the display part 7. When the image on the anterior ocular segment imaging element 625 is being displayed, the photographing mode shifts to the full manual mode, and the procedure proceeds to (S004). When the image on the imaging element 620 is being displayed, the photographing mode shifts to the full manual mode, and the procedure proceeds to (S008).

Finally, a case where the mode switching switch 8 is depressed during execution of the full auto mode will be described.

In (S501), energization to the Z electromagnetic clutch C1 and X electromagnetic clutch C2 is stopped to prevent the drive force from the drive parts D1 and D2 from being transmitted to the slide mechanism.

In (S502), it is determined which of the anterior ocular segment observation image and fundus observation image is being displayed on the display part 7. When the image on the anterior ocular segment imaging element 625 is being displayed, the photographing mode shifts to the full manual mode, and the procedure proceeds to (S004). When the image on the imaging element 620 is being displayed, the photographing mode shifts to the full manual mode, and the procedure proceeds to (S008).

With the configuration described above, even when the movable part 3 is electrically driven, relative positions of the alignment operation member 4 and ophthalmic part 6 with respect to the movable part 3 are not changed, so that a gravity center of the ophthalmic part 6 is not offset with respect to the movable part 3. Further, a relative position among the alignment operation member 4, display part 7, and photographing optical axis (ophthalmic part 6) which are arranged on substantially the same line is not changed, so that operability in the manual alignment is improved to enable fine alignment. Further, auto alignment and manual alignment is realized by one-stage movable part configuration, so that, as compared to the two-stage movable part configuration, an eccentric amount between the photographing optical axis and pupil center due to the fitting gap of the slide member is reduced, and space, cost, and weight are also reduced. In addition, even if a component of the drive part, such as a motor, fails, the apparatus of the invention can be used as an ophthalmologic apparatus without the auto alignment function since this state is the same as a state where the drive force is not transmitted to the slide mechanism by the setting of the drive force transmit switching unit.

Although the fundus camera is exemplified in the above embodiment, the present invention can be applied not only to the fundus camera, but also to various ophthalmologic apparatuses that require alignment between the eye E to be inspected and optical system.

As described above, according to the present embodiment, by selectively using the auto alignment and manual alignment, alignment accuracy between the eye to be inspected and ophthalmic part can be enhanced. Further, as compared to the one-stage movable part configuration only having a mechanical movable part or an electric movable part, it is possible to reduce a backlash amount to thereby enhance the alignment accuracy, unlike a conventional apparatus having a two-stage configuration in which the backlash amount is increased to affect the alignment accuracy.

That is, in the present embodiment, the slide mechanism is selectively moved by the electric movable part that can execute auto alignment and mechanical movable part that can execute fine manual alignment, whereby the one-stage movable part configuration is realized. Thus, a gravity center of the ophthalmic part is not offset with respect to the movable part during the manual alignment operation after the auto alignment. Further, a backlash amount is reduced as compared to a two-stage movable part configuration in which the electric movable part is placed on the mechanical movable part, thus enhancing the alignment accuracy between the eye to be inspected and ophthalmic part. Further, the alignment operation member, display part, optical axis of the photographing optical system, and eye to be inspected are arranged on the same line when the fine manual alignment is executed, so that manual operability is enhanced. In addition, as compared to the two-stage movable part configuration, space, cost, and weight are reduced. Further, even with a configuration excluding electric drive part for auto alignment, function of the mechanical movable part that can execute the manual alignment is not affected, so that, for example, even when a component of the drive part, such as a motor, fails, the apparatus of the invention can be used as an ophthalmologic apparatus without the auto alignment function by the time when the fault is repaired.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile (PVC), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-095266, filed May 2, 2014, which is hereby incorporated by reference herein in its entirety.

What is claimed is:

1. An ophthalmologic apparatus comprising:
   a movable unit including an examination unit and a manual operation member and configured to be movable with respect to a fixing unit in a horizontal direction;
   a drive unit that transmits electric drive force for horizontal movement of the movable unit; and
   a drive force transmit switching unit that switches whether or not to execute transmission of the electric drive force from the drive unit to the movable unit,
   wherein the movable unit moves by the electric drive force from the drive unit and the drive force transmit switching unit when the transmission of the electric drive force is executed, and the movable unit moves with the drive unit and the drive force transmit switching unit, by a manual drive force provided through the manual operation member when the transmission of the electric drive force is not executed, and
   wherein the movable unit is arranged by sharing a slide mechanism in a manual alignment of the examination unit for an eye to be inspected, the manual alignment being executed by using the manual operation member by an operator, and in an automatic alignment of the examination unit for the eye to be inspected, the automatic alignment being executed based on a relative position of the examination unit with respect to the eye to be inspected.

2. The ophthalmologic apparatus according to claim 1, further comprising:

an alignment detection unit that detects the relative position between the eye to be inspected and the examination unit; and a controller that controls the movable unit based on a detection result from the alignment detection unit.

3. The ophthalmologic apparatus according to claim 2, further comprising a determination unit that determines whether or not a value designating the detected relative position is equal to or more than a threshold value, wherein when it is determined that the value designating the detected relative position is equal to or more than the threshold value, the controller controls the drive force transmit switching unit to stop transmission of the electric drive force to the movable unit to stop movement of the movable unit.

4. The ophthalmologic apparatus according to claim 3, wherein the drive force transmit switching unit has a clutch that is energized to allow transmission of the electric drive force to the movable unit, and wherein switching of whether or not to execute transmission of the electric drive force is controlled by presence/absence of the energization to the clutch.

5. The ophthalmologic apparatus according to claim 2, further comprising:

a determination unit that determines whether or not a value designating the detected relative position is equal to or more than a threshold value, wherein when it is determined that the value designating the detected relative position is less than the threshold value, the controller controls the drive force transmit switching unit to execute transmission of the electric drive force to the movable unit to continue movement of the movable unit.

6. The ophthalmologic apparatus according to claim 1, further comprising:

a focus detection unit that detects a focus state with respect to the eye to be inspected; and a controller that controls the movable unit based on a detection result from the focus detection unit.

7. The ophthalmologic apparatus according to claim 6, further comprising:

a determination unit that determines whether or not a focus displacement amount of the detected focus state is equal to or less than a threshold value, wherein when it is determined that the focus displacement amount is equal to or less than the threshold value, the controller controls the drive force transmit switching unit to stop transmission of the electric drive force to the movable unit to stop movement of the movable unit.

8. The ophthalmologic apparatus according to claim 7, wherein the drive force transmit switching unit has a clutch that is energized to allow transmission of the electric drive force to the movable unit, and wherein switching to transmission stop of the electric drive force is executed by stop of energization to the clutch.

9. The ophthalmologic apparatus according to claim 1, further comprising a mode switching unit that switches between an auto alignment mode where alignment is automatically performed by the drive unit and a manual alignment mode where alignment is performed by an inspector, wherein the drive force transmit switching unit electrically switches, according to an output from the mode switching unit, whether or not to execute transmission of the electric drive force from the drive unit, the transmission being executed in the auto alignment mode and not being executed in the manual alignment mode.

10. The ophthalmologic apparatus according to claim 9, wherein the manual operation member is configured to align the eye to be inspected and the examination unit, wherein operating the manual operation member causes the movable unit to move with respect to the fixing unit in the horizontal direction, and wherein in the manual alignment mode, the inspector operates the manual operation member to perform the alignment.

11. The ophthalmologic apparatus according to claim 9, further comprising:

an absolute position detection unit that detects an absolute position of the movable unit; and a relative position detection unit that detects a moving amount of the movable unit, wherein in a state where the eye to be inspected is not detected, the auto alignment is performed under absolute position control, while in a state where the eye to be inspected is detected, the auto alignment is performed under relative position control.

12. The ophthalmologic apparatus according to claim 11, wherein a detection resolution of the relative position detection unit is higher than that of the absolute position detection unit.

13. The ophthalmologic apparatus according to claim 1, wherein the horizontal direction is a direction in a horizontal plane defined by an X-direction which is a width direction of the eye to be inspected and a Z-direction which is the direction approaching or separating from the eye to be inspected, and wherein the apparatus further comprises a Y-direction movable unit that is provided in the movable unit and configured to move the examination unit in a Y-direction perpendicular to the horizontal plane.

14. An ophthalmologic apparatus according to claim 1, wherein the movable unit includes a first movable system for a first movement of the movable unit in a first direction within the horizontal direction and a second movable system for a second movement of the movable unit in a second direction, the second direction intersecting with the first direction, wherein the drive unit includes a first drive system for a first transmission of electric drive force for the first movement and a second drive system for a second transmission of electric drive force for the second movement, wherein the drive force transmit switching unit includes a first drive force transmit switching system for switching whether or not to execute the first transmission and a second drive force transmit switching system for switching whether or not to execute the second transmission, and wherein the first movable system, the second movable system, the first drive system, the second drive system, the first drive force transmit switching unit, and the second drive force transmit switching unit are housed in one frame so as to be arranged in a horizontal plane located on the one frame.

15. An ophthalmologic apparatus according to claim 1, further comprising a control unit for controlling the drive force transmit switching unit so as to execute an autofocus operation for the eye to be inspected, after it is determined that the automatic alignment executed by using the electric drive force is completed, and so as to stop the transmission of the electric drive force to make the manual alignment for the eye to be inspected possible, after it is determined that the autofocus operation is completed.

16. An ophthalmologic apparatus according to claim 1, wherein the movable unit includes a frame, and
wherein when the frame moves in the horizontal direction relative to the fixing unit, so too does the manual operation member.

17. An ophthalmologic apparatus according to claim 1, wherein the movable unit, including the manual operation member, moves relative to the fixing unit in the horizontal direction by the electric drive force from the drive unit and the drive force transmit switching unit when the transmission of the electric drive force is executed, and the movable unit, including the manual operation member, moves with the drive unit and the drive force transmit switching unit relative to the fixing unit in the horizontal direction, by a manual drive force provided through the manual operation member when the transmission of the electric drive force is not executed.

18. An ophthalmologic apparatus according to claim 1, wherein the movable unit is arranged as one-stage part by sharing the slide mechanism.

\* \* \* \* \*